United States Patent [19]

May

[11] 4,065,525
[45] Dec. 27, 1977

[54] INHIBITION OF CRYSTALLIZATION OF O-ETHYL-O-(4-NITROPHENYL)-PHENYL-PHOSPHONOTHIOATE

[75] Inventor: Ralph Forrest May, Wilmington, Del.

[73] Assignee: E. I. Du Pont de Nemours and Company, Wilmington, Del.

[21] Appl. No.: 723,956

[22] Filed: Sept. 16, 1976

[51] Int. Cl.² .................................................. C07F 9/40
[52] U.S. Cl. .................................. 260/989; 260/954; 260/973
[58] Field of Search ................ 260/989, 990, 973, 954

[56] References Cited

U.S. PATENT DOCUMENTS

| | | | |
|---|---|---|---|
| 2,503,390 | 4/1950 | Jelinek | 260/954 X |
| 3,327,026 | 6/1967 | Shindo et al. | 260/973 |
| 3,896,192 | 7/1975 | Sehring et al. | 260/982 |

*Primary Examiner*—Richard L. Raymond

[57] ABSTRACT

Crystallization of O-ethyl-O-(4-nitrophenyl)-phenylphosphonothioate is inhibited by maintaining therein between about 6 and about 12% by weight of bis-(O-4-nitrophenyl)-phenylphosphonothioate, optionally standardizing the active ingredient content to a predetermined level, preferably 80%, and or optionally destroying seed crystals present in the inhibited composition in order to extend the effectiveness of the crystallization inhibitor.

9 Claims, No Drawings

INHIBITION OF CRYSTALLIZATION OF O-ETHYL-O-(4-NITROPHENYL)-PHENYLPHOSPHONOTHIOATE

BRIEF SUMMARY OF THE INVENTION

This invention relates to a method of inhibiting crystallization of O-ethyl-O-(4-nitrophenyl)-phenyl-phosphonothioate (otherwise known as EPN) by maintaining therein between about 6 and about 12% by weight of bis-(O-4-nitrophenyl)-phenylphosphonothioate (also known as bis-EPN).

BACKGROUND OF THE INVENTION

EPN is an insecticide widely used in agricultural applications. That compound and its use is claimed by Jelinek in U.S. Pat. No. 2,503,390. Jelinek prepared EPN by reacting a thionobenzene phosphonyl dichloride with sodium ethylate to give ethylthionobenzene phosphonyl monochloride which was then reacted with sodium p-nitrophenate to give EPN. The EPN prepared by Jelinek was an oily liquid having a light yellow color and was indicated by Jelinek to be not highly refined.

Shindo et al. in U.S. Pat. No. 3,327,026 describes a process for preparing EPN in which 2-methyl-5-ethylpyridine is used as a catalyst so as to inhibit production of by-products, such as bis-(O-ethyl)-phenylphosphonothioate and bis-(O-4-nitrophenyl)-phenylphosphonothioate.

Technical EPN which is currently available commercially is a light tan to brown composition which typically contains from 85 to 90% EPN, the rest being by-products, side reaction products and impurities. Pure EPN has a melting point of approximately 36° C (e.g. see U.S. Pat. No. 3,896,192, column 7, lines 54–55), and under normal storage or warehouse conditions, particularly in the fall, winter or early spring, technical EPN will solidify in part, or entirely, inside the shipping container due to crystallization of the EPN. This poses the obvious inconvenience that a formulator who wishes to use the technical EPN to prepare an agricultural formulation must melt the material prior to removal from the drum, or must flush it from the drum with hot solvent, or must open the drum in order to remove the active ingredient as a solid or a solid-laden slush. In addition to the inconvenience of such handling, there is a health hazard because of EPN toxicity, particularly if drums are opened and the EPN is removed as a solid or slush.

It is, therefore, desirable to prevent the crystallization of solid EPN in shipping containers or to delay or inhibit such crystallization for a sufficient time period so that the user who receives an EPN shipment will be able to handle the material as a liquid before the onset of undesirable crystallization. True lowering of the EPN crystallization temperature could be achieved by the addition of solvents in accordance with the normal laws of physical chemistry. However, the solvents that have been used in pursuing the problem leading to the present invention were not very effective, and large amounts would be required to keep EPN liquid at, for example, 0° C. It is, therefore, desirable to add to the technical EPN a crystallization inhibitor. As is known to those skilled in the art, a crystallization inhibitor is a material which does not prevent crystallization by virtue of modifying the true crystallization or freezing point or by virtue of acting as a solvent, but rather is a material which interferes with the nucleation of crystals and, once crystals have nucleated, prevents or inhibits or slows down the further growth of crystals in the liquid medium. As is also known in this art, one cannot predict which material would serve as a crystallization inhibitor from equations or known laws.

DETAILED DESCRIPTION OF THE INVENTION

The present invention overcomes the disadvantages and difficulties encountered in the prior art by providing a method for inhibiting crystallization of EPN at temperatures in the range between $-6°$ and $25°$ C comprising maintaining in the EPN between about 6 and about 12% by weight of bis-EPN. The temperature range is given for practical purposes only; obviously crystallization will likewise be inhibited at higher temperatures. Likewise for practical purposes, usually a bis-EPN content in the range between about 6 and about 9% by weight is sufficient to inhibit crystallization of EPN effectively. As bis-EPN is ineffective as an insecticide, adding a great deal of it to EPN will reduce the insecticidal activity of the latter. In the event that one were to use less than 6% by weight of bis-EPN, inhibition of crystallization of EPN at temperatures such as 0° C or 15° C would not be obtained to a satisfactory degree.

In the case of EPN, it is also often desirable to adjust or standardize the strength of the technical EPN so as to provide the user with a composition that always has the same active ingredient, in liquid form, at a strength level convenient for further formulation to insecticidal emulsifiable concentrates. Adjustment or standardization of the strength of the technical EPN may be accomplished by adding, to the combined EPN and bis-EPN, a solvent such as an aromatic hydrocarbon or a cyclic ketone so as to standardize the EPN content at about 80% by weight. Although such adjustment is a preferred feature of the invention, it is not a critical one.

Once the crystallization inhibitor of the present invention, bis-EPN, is present in the EPN in the appropriate amount and, if desired, the EPN strength has been standardized by addition of a solvent, the crystallization inhibition can be further improved and the time of the product in the liquid state can be further extended if procedures are employed to destroy, dissolve, melt, or otherwise inactivate any seed crystals which would represent the starting point for further crystal growth. Thus, the optional destruction of seed crystals in compositions containing a crystallization inhibitor may make the inhibitors particularly effective. The present invention, therefore, deals with a method of inhibiting the crystal growth of EPN, of optionally standardizing the active ingredient content to a predetermined level, preferably 80%, and of optionally destroying seed crystals present in the inhibited composition in order to extend the effectiveness of the crystallization inhibitor.

Solvents to be used to standardize EPN should be aprotic, nonbasic, nonparaffinic, nonphytotoxic organic liquids, e.g. aromatic xylene and naphthalene type solvents, comprising the following hydrocarbons:

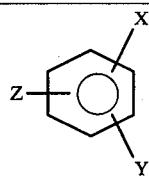

wherein X and Y can be the same or different and can be H, CH₃, CH₃CH₂—, (CH₃)₂CH—, CH₃CH₂CH₂— Z can be CH₃—, CH₃CH₂—

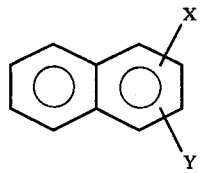

Y, X=H, CH₃, —CH₂CH₃, etc.

Other solvents may be esters, such as ethyl acetate, ketones, especially cyclic ketones such as cyclohexanone chlorinated hydrocarbons, phenol, acetonitrile, etc.

The preferred alkylaromatic solvents to standardize technical EPN to an 80% active content are xylene-range aromatic hydrocarbons and naphthas having a flash point (Tag closed cups) of about 27° C or higher and preferably 38° to 50° C. These solvents are mixtures of components such as ethylbenzenes, xylenes, isopropylbenzenes, methylethyl benzenes, trimethylbenzenes, etc. Typically, they contain from 90 to 100 volume percent aromatics and have a distillation range from about 130° to 165° C (initial distillation temperature) to about 140° to 200° C (dry point).

The bis-EPN content may be controlled at 6% or above in a variety of ways. When the EPN process is started, a heel of benzenephosphorus thiodichloride may be charged first and reacted with p-nitrophenol or sodium p-nitrophenolate to produce bis-EPN. Additional benzenephosphorus thiodichloride ("BPT", )

is added and EPN is produced in the normal fashion by adding ethanol, p-nitrophenol (or sodium p-nitrophenolate) and acid acceptors. Alternatively, the EPN process may be modified to obtain high bis-EPN content, for example, by using an excess of p-nitrophenol or metal p-nitrophenolate. On the other hand, bis-EPN can be produced and isolated, and added back to EPN, at the end of the normal EPN reaction, in accordance with the amount needed to control the bis level at 6% or above.

When the EPN is heated, to obtain destruction of seed crystals, the temperature should be above about 40° C. The upper limit of temperature is set by the stability of EPN, and 60° C represents a sensible maximum. Regarding the destruction of seed crystals, what is important is not the heating step per se, but that when the container is filled and then closed, the entire closed package, drum and contents be above 40° C.

In the examples the follow, percentages are by weight, and "Tenneco Oil" referred to is a xylene-range aromatic solvent having the following specifications:

Table 1

| Properties | Specification | ASTM Test Method |
|---|---|---|
| Specific Gravity, 15.56/15.56° C | 0.860–0.875 | D-891–59 |
| Acidity | No free acid | D-847–47 |
| Doctor | Sweet | D-484–71 |
| Copper Corrosion | Negative | D-849–47 |
| Sulphur Compounds | Free of H₂S & SO₂ | D-853–71 |
| Flash, TCC, Minimum, ° C | 38 | D-56–71 |
| Kauri-Butanol Value, Minimum | 92 | D-1133–61 |
| Aromatics, Volume % Min. | 95 | G.C. |
| Distillation Range, Initial Distillation Temperature | Not below 143° C. | |
| Dry Point | Not above 171° C. | |

EXAMPLE 1

In order to demonstrate the effectiveness of bis-EPN as a crystallization inhibitor, the following tests are presented.

a. Technical EPN containing 88.3% EPN and 1.63% bis-EPN is seeded with at least one crystal of pure EPN and placed at 0° C. In one day the material is 100% solid.

b. Technical 88.3% EPN and 1.63% bis-EPN is diluted to 82.1% EPN by the addition of 7.0% Tenneco Oil to the 88.3% EPN. The samples are seeded as aforesaid and placed at 0° C. The sample is 85% solid in one week.

c. The same technical EPN is diluted by adding 6.0% of bis-EPN to the technical EPN. This brings the total bis content to 7.63% and the EPN content to 83.3%. The sample is seeded as aforesaid and placed at 0° C. No solid is observed after storage for 15 days.

EXAMPLE 2

To show the effect of bis-EPN and EPN content on solid formation in samples at 0° C, seeded as aforesaid, increasing amounts of additional bis-EPN are added to technical 88.3% EPN, containing 1.63% bis-EPN. The following results are observed:

Table 2

| % Total Bis-EPN | % EPN | % Solids after 15 days |
|---|---|---|
| 1.63 | 88.3 | 100 |
| 2.63 | 87.3 | 90 |
| 3.63 | 86.3 | 70 |
| 4.63 | 85.3 | 30 |
| 5.63 | 84.3 | 10 |
| 6.63 | 83.3 | 10 |
| 7.63 | 82.3 | 1 |
| 8.63 | 81.3 | 0 |

EXAMPLE 3

To show the effect of increased bis-EPN content in the presence of Tenneco Oil, 88.1% technical EPN, containing 1.33% bis-EPN, is blended with 5% Tenneco Oil and increasing amounts of additional bis-EPN. The samples are seeded as aforesaid and placed at 0° C. The following results are presented after 8 days:

Table 3

| % Total Bis-EPN | % Tenneco Oil | % EPN | % Solids |
|---|---|---|---|
| 1.33 | 0 | 88.1 | 95 |
| 1.33 | 5 | 83.1 | 75 |
| 2.33 | 0 | 87.1 | 95 |
| 2.33 | 5 | 82.1 | 50 |

Table 3-continued

| % Total Bis-EPN | % Tenneco Oil | % EPN | % Solids |
| --- | --- | --- | --- |
| 3.33 | 0 | 86.1 | 90 |
| 3.33 | 5 | 81.1 | 20 |
| 4.33 | 0 | 85.1 | 90 |
| 4.33 | 5 | 80.1 | 10 |
| 5.33 | 0 | 84.1 | 20 |
| 5.33 | 5 | 79.1 | 5 |
| 6.33 | 0 | 83.1 | 10 |
| 6.33 | 5 | 78.1 | 1 |
| 7.33 | 0 | 82.1 | 5 |
| 7.33 | 5 | 77.1 | 1 |
| 8.33 | 0 | 81.1 | 1 |
| 8.33 | 5 | 76.1 | 0 |
| 9.33 | 0 | 80.1 | 1 |
| 9.33 | 5 | 75.1 | 0 |

What is claimed is:

1. A method of inhibiting crystallization of O-ethyl-O(4-nitrophenyl)-phenylphosphonothioate at temperatures in the range between (−) 6° C. and 25° C. comprising maintaining therein between about 6 and about 12% by weight of bis-(O-4-nitrophenyl)-phenylphosphonothioate.

2. The method of claim 1 wherein the level of said bis compound is maintained in the range between about 6 and about 9% by weight.

3. The method of claim 2 wherein the amount of the O-ethyl-O-(4-nitrophenyl)-phenylphosphonothioate is adjusted to about 80% by weight by adding thereto an aprotic, nonbasic, nonparaffinic, nonphytotoxic, organic solvent.

4. The method of claim 3 wherein said organic solvent is an alkylaromatic hydrocarbon having a flash point of at least about 27° C. and a distillation range between about 130° C. and 200° C.

5. The method of claim 4 wherein the product prepared thereby is, during packaging thereof, maintained at a temperature between about 40° C. and the decomposition temperature of O-ethyl-O-(4-nitrophenyl)-phenylphosphonothioate.

6. The method of claim 5 wherein prior to packaging sufficient bis-(O-4-nitrophenyl)-phenylphosphonothioate is added to O-ethyl-O-(4-nitrophenyl)-phenylphosphonothioate so as to maintain said bis compound at said level.

7. The method of claim 5 wherein prior to packaging said level of said bis compound is produced in situ in a process comprising reacting thionobenzenephosphonyl dichloride with an ethoxylating agent selected from ethanol and a metal ethoxide and a phenoxylating agent selected from p-nitrophenol and a metal p-nitrophenolate.

8. The method of claim 7 wherein a portion of the thionobenzenephosphonyl dichloride is reacted with a portion of said phenoxylating agent prior to reaction of said portion of said dichloride with said ethoxylating agent.

9. The method of claim 7 wherein a sufficient excess of said phenoxylating agent is reacted with said dichloride so as to maintain said level of said bis compound.

* * * * *